United States Patent
Stefanovsky et al.

[11] Patent Number: 6,081,934
[45] Date of Patent: Jul. 4, 2000

[54] LASER EYE GOGGLE

[75] Inventors: David W. Stefanovsky, Willowick, Ohio; Ronald G. Wheeland, Fair Oaks, Calif.

[73] Assignee: Stefanovsky & Associates, Inc., Willowick, Ohio

[21] Appl. No.: 09/027,393

[22] Filed: Feb. 20, 1998

Related U.S. Application Data

[60] Provisional application No. 60/040,951, Mar. 18, 1997.

[51] Int. Cl.[7] ........................................................ A61F 9/02
[52] U.S. Cl. ................................................ 2/431; 128/858
[58] Field of Search ................................... 2/431, 6.7, 6.3, 2/432, 426; 128/858

[56] References Cited

U.S. PATENT DOCUMENTS

| | | | |
|---|---|---|---|
| 3,791,721 | 2/1974 | Helfrich | 351/44 |
| 4,024,405 | 5/1977 | Szot | 250/516 |
| 4,122,847 | 10/1978 | Craig | 128/858 |
| 4,462,661 | 7/1984 | Witt | 350/331 R |
| 4,635,625 | 1/1987 | Teeple | 128/163 |
| 4,703,522 | 11/1987 | Schurle et al. | 2/432 |
| 4,835,796 | 6/1989 | Wiedner | 2/431 |
| 4,917,481 | 4/1990 | Koechner | 350/363 |
| 5,016,292 | 5/1991 | Rademacher | 2/431 |
| 5,073,324 | 12/1991 | Beudet | 264/255 |
| 5,469,229 | 11/1995 | Greenbaum | 351/44 |
| 5,708,490 | 1/1998 | Wieczorek | 351/47 |
| 5,802,622 | 9/1998 | Baharad et al. | 2/434 |
| 5,918,600 | 7/1999 | Durette | 128/857 |

FOREIGN PATENT DOCUMENTS 588384  3/1994  Germany .................................. 2/431

OTHER PUBLICATIONS

Gerald Schlenker, Fact Sheet for Laser Safety, www.uky.edu/FiscalAffairs/Environmental/radiation/laser, p. 1, Mar. 11, 1999.
Gerald Schlenker, Fact Sheet for Laser Safety, www.uky.edu/FiscalAffairs/Environmental/radiation/laser, p. 1, Mar. 11, 1999.

*Primary Examiner*—Diana Oleksa
*Assistant Examiner*—Kate Moran
*Attorney, Agent, or Firm*—Calfee, Halter & Griswold LLP

[57] ABSTRACT

An extra-ocular laser eye goggle (10) includes first and second eye shields (15) which are adapted to be mounted on and cover the eyes of a subject during a facial laser surgery. Each eye shield (15) is formed from a non-light transmissive material and includes an exterior surface (20) which diffuses a laser upon impact such that the subject is not injured. A seal member (35) is provided on each eye shield (15) which provides a sealing interface between the eye shields and the subject such that light is prohibited from passing between the eye shields (15) and the subject.

19 Claims, 4 Drawing Sheets

LASER EYE GOGGLE

This application claims benefit of provisional application Ser. No. 60/040,951 filed Mar. 18, 1997.

BACKGROUND OF THE INVENTION

The present invention relates to the protective eye wear arts. It finds particular application in conjunction with extraocular laser eye goggles for protecting eyes of a subject undergoing facial laser surgery and will be described with particular reference thereto. However, it is to be appreciated that the present invention will also find application in conjunction with other applications in which eyes must be protected from laser light exposure.

During a dermatologic or plastic surgery, eye goggles are worn by subjects to protect their eyes from potential optical hazards associated with surgical lasers. For example, class 4 surgical lasers include CO2, argon, argon dye, flashlamp dye, frequency doubled YAG, ruby, and alexandrite lasers. Exemplary protective eye wear frequently used during facial surgery include suntan goggles, swimming goggles, or black felt. Suntan and swim goggles are typically formed from a plastic or polymer compound material which can withstand only an incidental or split second laser impact.

When a suntan or swim goggle is impacted with a flashlamp dye laser, the goggle ignites in a blue flame. This creates a potential fire hazard if the subject is under general anesthesia breathing through an oxygen line. When exposed to a CO2 laser, the laser causes a hole to be burned all the way through the goggle after only a period of about eight seconds as well as producing a potentially toxic smoke having an irritating smell. When exposing black felt to a laser impact, its threads can smolder and burn.

In accordance with the present invention, a laser eye goggle is provided which can withstand significant laser impacts to effectively protect the eyes of a subject.

SUMMARY OF THE INVENTION

A new and improved laser eye goggle for facial laser surgery is provided. The laser eye goggle is worn by a subject and includes two eye shields each covering one eye of the subject. The eye shields are formed of a non-light transmissive material and has an exterior surface which diffuses a laser beam upon impact such that the laser eye goggle can withstand a continuous laser beam impact without causing injury to the subject.

In accordance with a more limited aspect of the present invention, a sealing member is provided on each of the first and second eye shields which provide a resilient interface between each eye shield and the subject. The sealing member is adapted to engage the subject such that light is prohibited from passing between the eye shields and the subject.

In accordance with a more limited aspect of the present invention, the eye shield is formed from a surgical grade stainless steel which has a matte finish.

One advantage of the present invention is that the laser eye goggle is comfortably worn by a subject and can withstand a continuous impact from at least a class 4 laser without causing injury to the subject.

Still other advantages and benefits of the invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 3:
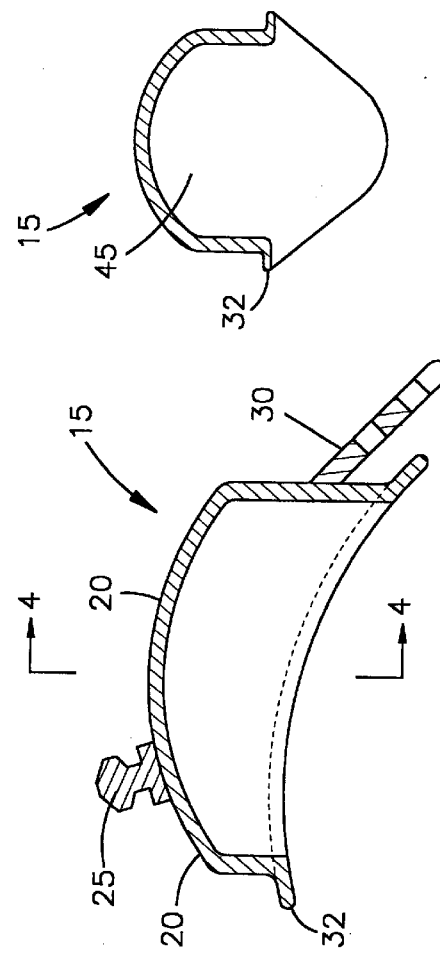
FIG. 3 is a cross section of the eye cup shown in FIG. 2.
Figure 1:
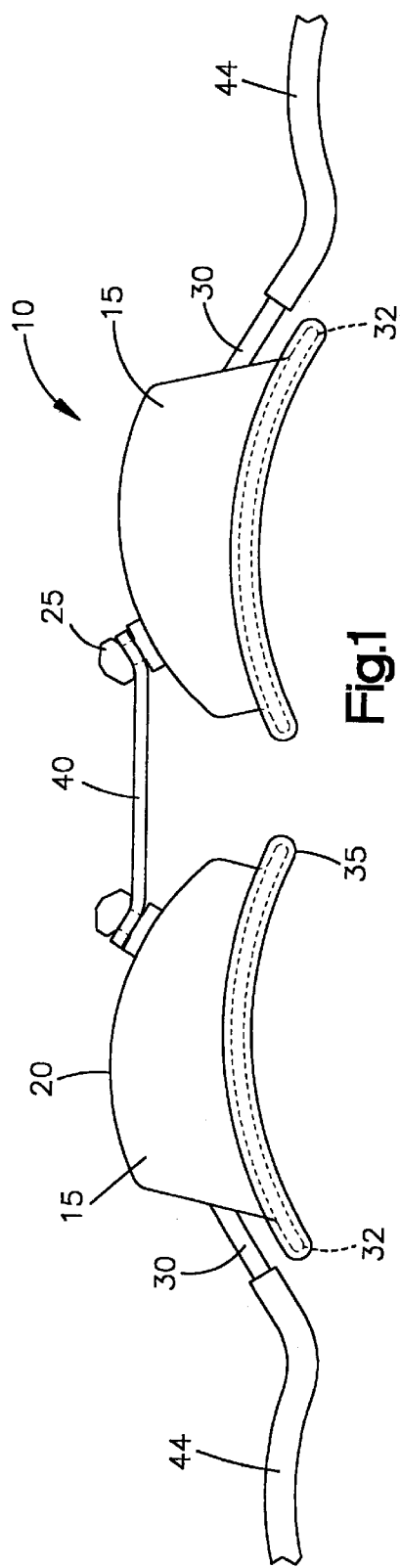
FIG. 1 is a side view of a laser eye goggle in accordance with the present invention.
Figure 2:
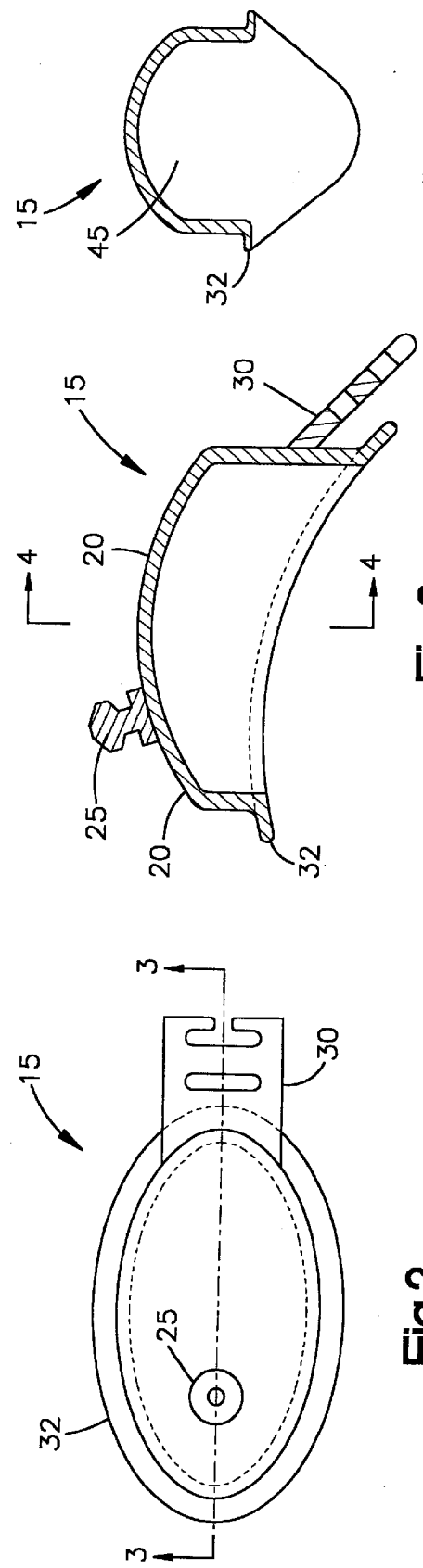
FIG. 2 is a top view of an eye cup in accordance with the present invention.

With reference to FIGS. 1, 2, and 3, a laser eye goggle 10 includes first and second eye cups or shields 15. Each eye cup 15 is substantially identical to each other and are adapted to comfortably fit the contour and curvature of a subject's face and eye orbit such that the eyes of the subject are enclosed by the eye cups 15. The eye cups 15 are made of a material which can withstand a direct and continuous laser impact without being damaged and without excessive heating. Preferably, the material is stainless steel which meets surgical steel standards. Alternately, other materials may be used which can withstand a laser impact and does not react with human skin when exposed to a laser.

The eye cups 15 do not transmit light and, thus, prohibit a laser from passing therethrough. An external surface 20 diffuses and/or scatters laser light such that the intensity and concentration of an impacting laser are substantially reduced. A diffused laser is less likely to damage the goggle 10, the subject's eyes, or periorbital skin. Portions of an impacting laser are further absorbed by the steel eye cups 15 and reflected as heat to further lessen any harmful effects and brightness associated with lasers which can cause permanent injury or blindness to a subject. The external surface 20 is textured to render a laser light incoherent and to distribute its energy over a wide spectrum range and area.

The steel of the eye cups 15 is annealed and then stamped to form. The external surface 20 preferably includes a contoured shape which provides for additional diffusion of a laser impact and reduces reflectivity. Of course, other shapes can be used as desired. All burrs are removed from each eye cup 15 by, for example, sanding and grinding the steel. The eye cups 15 are then bead or sand blasted with a 40 to 60 grit material to provide a matte finish to the external surface 20 to further promote the diffusion and scattering of a laser light impact.

With further reference to FIGS. 1 and 3, each eye cup 15 includes a mounting flange or lip 32 extending around the eye cup 15. The flange 32 is adapted to receive an orbital skin seal member 35 attached to and enclosing the edges of the flange 32. The seal member 35 is formed from a soft and flexible material such as molded rubber to provide a resilient interface between each eye cup and the skin of a subject and provides a comfortable fit. The seal member 35 is formed to minimize pinching or pulling on the fragile periorbital skin and is sufficiently resilient to adapt to the contours of the subject to prevent light from entering the subject's eye between the seal member 35 and the skin. Preferably, the seal member is white so that it has anti-light absorbing characteristics. Of course, other types of seals can be used which have anti-light absorbing characteristics.

With reference to FIG. 1, a nose bridge connector nipple 25 is attached to each eye cup 15 along with a head strap connector 30. Preferably, they are made of the same material as the eye cups 15b and each include a laser diffusing surface. The nose bridge connector 25 and head strap connector 30 are attached by welding or other process which sufficiently secures the connectors to the eye cup 15.

Figure 5A:
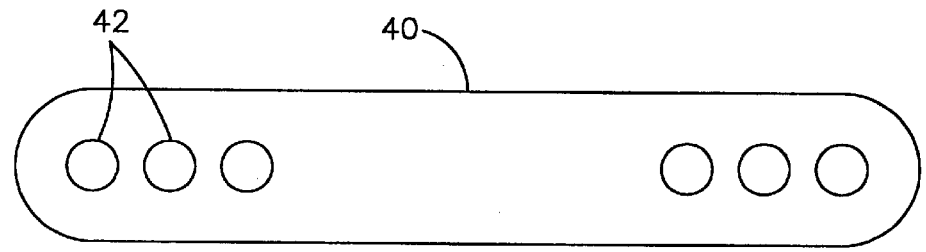
FIGS. 5A and 5B illustrate an adjustable nose bridge connector in accordance with the present invention.
Figure 5B:
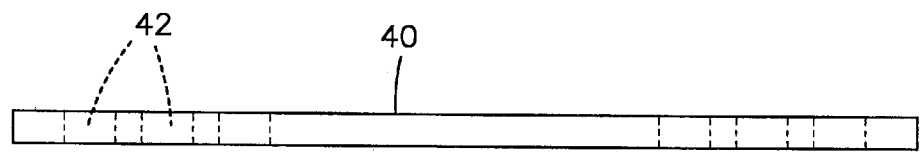

With reference to FIGS. 1, 5A, and 5B, an adjustable nose bridge strap 40 attaches to the nose bridge connector 25 at each end through any one of a plurality of connection holes 42. The bridge strap 40 connects the two eye cups 15 and maintains the eye cups a selected distance from each other. The nose bridge strap 40 is preferably made from a 40 durometer barium filled silastic silicon material which is pressure injected into a mold. The strap 40 is sufficiently pliable to be stretched over and connected to the nose bridge connector 25 such that the eye goggle may accommodate different facial features and nose sizes. Of course, the nose bridge strap may have any desired ridgedness for a desired fit. The material forming the nose bridge strap 40 is selected to have properties which do not absorb light such as including a white color.

With further reference to FIG. 1, a head strap 44 is attached to the head strap connector 30 and is used to mount the goggles 10 to a subject's head. Preferably, the adjustable head strap 44 is made of an elastic material such that it stretches to fit different head sizes. Alternately, it may secure the goggles 10 to a subject's ears.

Figure 4:
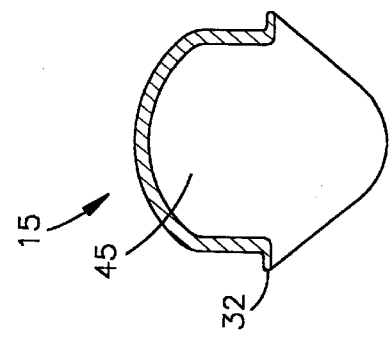
FIG. 4 is a cross section of the eye cup shown in FIG. 3.

With reference to FIG. 4, the eye cup 15 defines an inner cavity 45 such that the inner surface of the eye cup does not contact the eye of the subject and is preferably sized to receive wet cottonoids or gauze during surgery. The wet cottonoids or other moisture retaining material provide additional cooling and distribution of heat generated from a direct laser impact on the exterior surface 20 of the eye cup 15.

Figure 6:
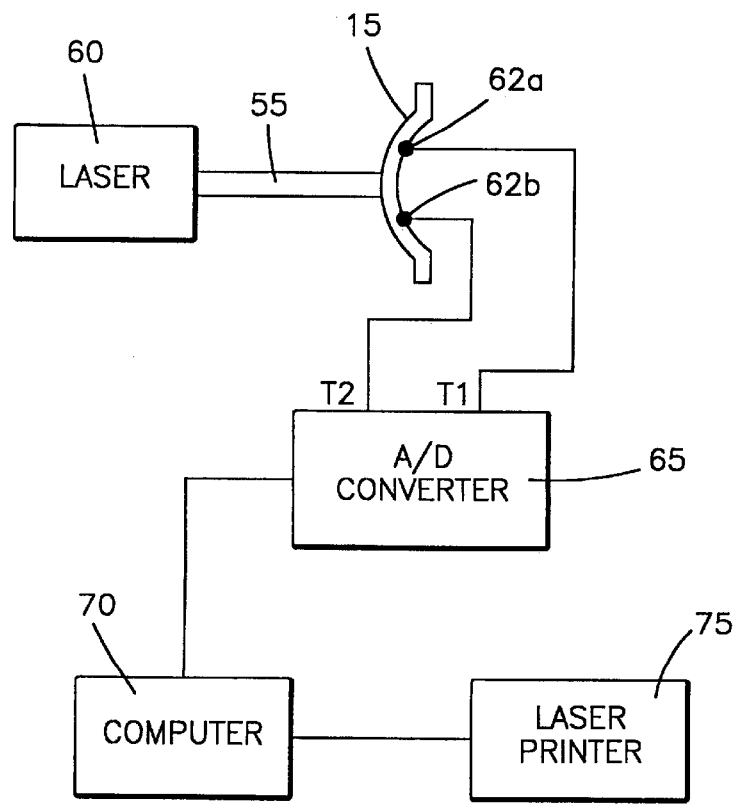
FIG. 6 illustrates temperature measurements made while exposing the present invention to a continuous laser impact.
Figure 7:
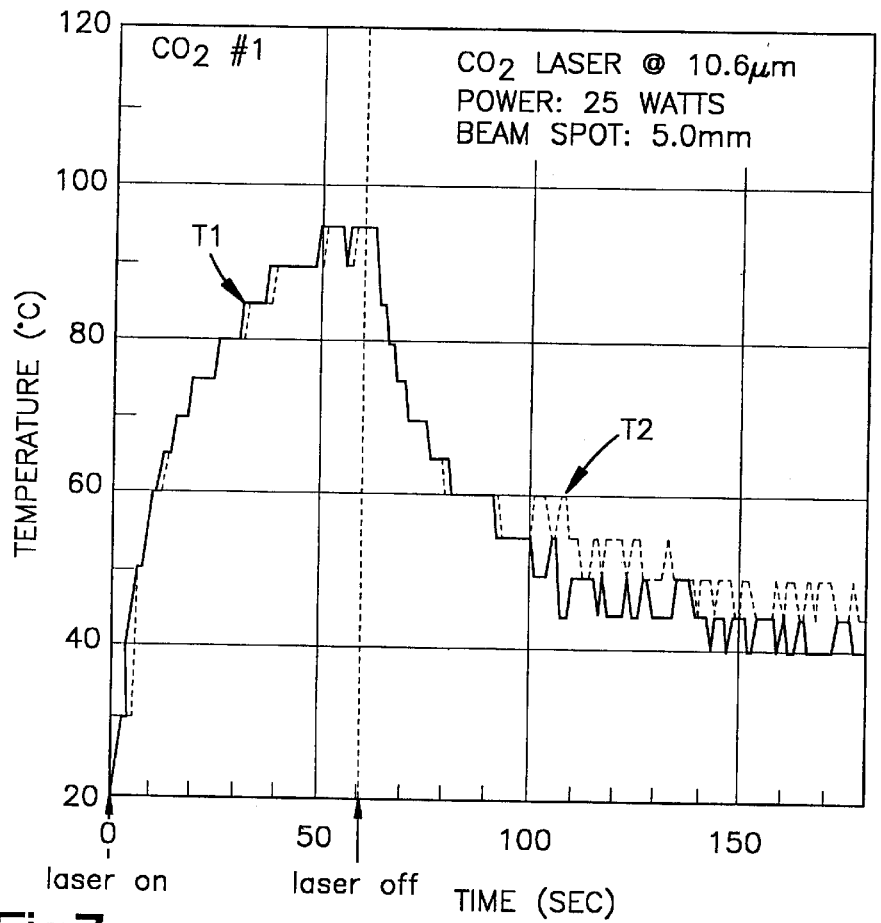
FIG. 7 is a temperature graph of the measurements of FIG. 6.

With reference to FIGS. 6, 7, 8 and 9, the laser eye goggle 10 was laser impact tested for up to 60 seconds with the following lasers: argon, YAG, CO2, and flashlamp pumped dye and alexandrite lasers. FIG. 6 illustrates the eye cup 15 being exposed to about a 5 mm continuous laser beam 55 generated by a laser 60 at 10.6 $\mu$m having a power of 25 watts. The inner surface (e.g., the subject side) temperature of the eye cup 15 is measured by two temperature probes 62a and 62b which measure temperatures T1 and T2, respectively. An analog/digital converter 65 receives the temperature readings which are stored and printed by a computer 70 on a printer 75. FIG. 7 illustrates a graph showing the measurements taken for temperatures T1 and T2 of the inner surface eye cup temperature over time in seconds of a continuous laser impact.

Figure 8:
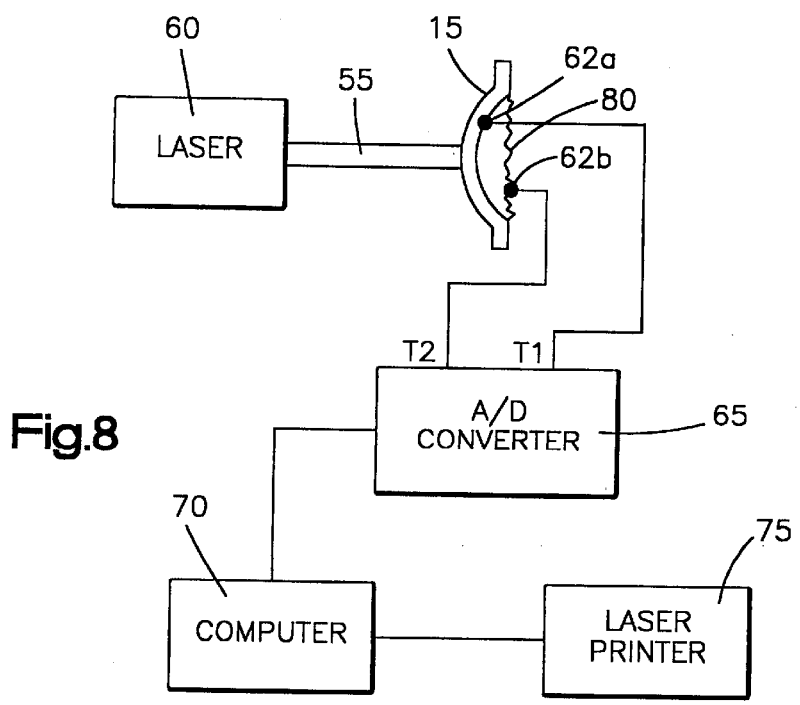
FIG. 8 illustrates temperature measurements made while exposing the present invention including a wet cottonoid to a continuous laser impact; and, FIG. 9 is a temperature graph of the measurements of FIG. 8.
Figure 9:
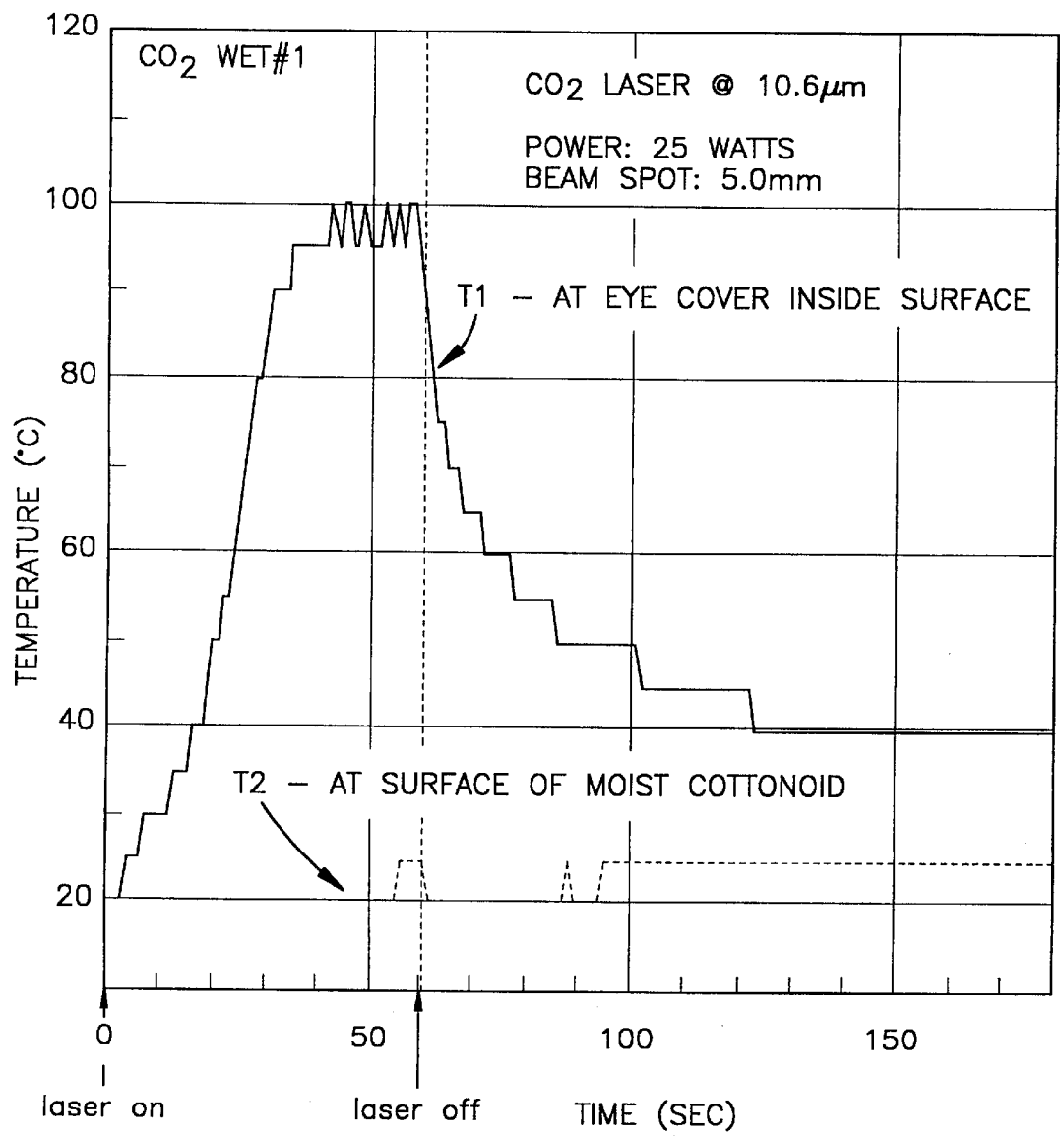

With reference to FIG. 8, the same measurements were taken except with a wet cottonoid 80 inserted into the inner cavity of the eye cup 15 and T2 being the temperature of the wet cottonoid. FIG. 9 illustrates the temperatures T1 and T2 during a continuous laser impact.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. An extra-ocular laser eye goggle for protecting eyes of a subject from a laser during a facial laser surgery comprising:

first and second eye cups each for covering an eye of a subject, the first and second eye cups being optically non-transmissive and including a matted outer surface for diffusing a laser light to be incoherent such that the first and second eye cups withstand a continuous impact from at least a class 4 laser;

a bridge connecting the first and second eye cups;

an adjustable strap connected to the first and second eye cups and being adapted for securing the first and second eye cups to the subject; and a sealing member on each of the first and second eye cups for providing a resilient interface between each eye cup and the subject, the sealing member being adapted to engage the subject such that light is prohibited from passing between the eye cups and the subject.

2. The laser eye goggle as set forth in claim 1 wherein the first and second eye cups are formed from surgical grade stainless steel.

3. The laser eye goggle as set forth in claim 1 wherein the class 4 lasers include one of CO2, argon, argon dye, flash lamp dye, frequency doubled YAG, ruby, and alexandrite lasers.

4. The laser eye goggle as set forth in claim 1 wherein the sealing member being formed of a substantially anti-light absorbing material.

5. The laser eye goggle as set forth in claim 1 wherein the first and second eye cups each include an inner cavity for receiving a moisture retaining material such that the moisture retaining material is maintained between each eye cup and an associated eye.

6. The laser eye goggle as set forth in claim 1 wherein the first and second eye cups being formed of a material which can withstand a direct continuous impact from at least a class 4 laser for at least 10 seconds without causing injury to a subject wearing the laser eye goggle.

7. An eye goggle for protecting eyes of a subject during a facial laser surgery comprising:

an eye shield formed to cover the eyes of the subject, the eye shield prohibiting transmission of light and including an outer surface which scatters a laser beam upon impact such that the eye and adjacent skin of the subject are protected; and a seal on the eye shield being an interface between the eye shield and the subject, the seal being adapted to engage the subject and substantially occlude transmission of light from passing between the eye shield and the subject.

8. The eye goggle as set forth in claim 7 wherein the eye shield is curved defining an inner cavity adapted to receive an eye of a subject such that the eye does not contact the eye shield.

9. The eye goggle as set forth in claim 7 wherein the eye shield having a sufficient thickness to absorb a portion of an impacting laser and reflect the absorbed portion as heat.

10. The eye goggle as set forth in claim 7 wherein the eye shield is formed for withstanding a continuous impact from at least a class 4 laser for at least 10 seconds.

11. The eye goggle as set forth in claim 10 wherein the eye shield is formed from a surgical grade stainless steel.

12. The eye goggle as set forth in claim 7 wherein the seal is formed of a resilient material which is adapted for providing a resilient engagement between the eye shield and a subject.

13. The eye goggle as set forth in claim 7 wherein the eye shield includes two eye covers, the two eye covers being connected by a bridge such that each eye cover is adapted to cover one eye of the subject.

14. The eye goggle as set forth in claim 13 further including an adjustable strap connecting the two eye shields, the adjustable strap being for securing the two eye shields to a subject.

15. The eye goggle as set forth in claim 7 wherein the outer surface is a matte surface.

16. An extra-ocular laser eye goggle for protecting eyes of a subject from a laser during a facial laser surgery, the laser eye goggle including a first eye shield and a second eye shield connected to each other by a bridge and being configured to be worn on the subject where each eye shield covering one eye of the subject, the improvement comprising:

the first and second eye shields being formed of a non-light transmissive material having an exterior surface which diffuses a laser beam upon impact such that the first and second eye shields can be continuously exposed to a laser beam without causing injury to the subject.

17. The extra-ocular laser eye goggle as set forth in claim 11 wherein the first and second eye shields are formed from a stainless steel composition.

18. The extra-ocular laser eye goggle as set forth in claim 11 further including an interface on each of the first and second eye shields, the interface adapted for resiliently engaging the first and second eye shields to the subject and substantially occlude transmission of light from passing between the eye shields and the subject.

19. The extra-ocular laser eye goggle as set forth in claim 11 further wherein the exterior surface includes a matte surface.

* * * * *